US012116705B2

(12) United States Patent
Steinhilber (10) Patent No.: US 12,116,705 B2
(45) Date of Patent: Oct. 15, 2024

(54) METHOD FOR PRODUCING A BRAIDED SINGLE-FILAMENT STENT, DEVICE AND BRAIDING CORE FOR THIS PURPOSE, AND BRAIDED SINGLE-FILAMENT STENT

(71) Applicant: STEBO Sondermaschinenbau GmbH & Co. KG, Bodelshausen (DE)

(72) Inventor: Helmut Steinhilber, Bodelshausen (DE)

(73) Assignee: STEBO SONDERMASCHINENBAU GMBH & CO. KG, Bodelshausen (DE)

( * ) Notice: Subject to any disclaimer, the term of this patent is extended or adjusted under 35 U.S.C. 154(b) by 620 days.

(21) Appl. No.: 17/423,682

(22) PCT Filed: Jan. 17, 2020

(86) PCT No.: PCT/EP2020/051172
§ 371 (c)(1),
(2) Date: Jul. 16, 2021

(87) PCT Pub. No.: WO2020/148444
PCT Pub. Date: Jul. 23, 2020

(65) Prior Publication Data
US 2022/0119997 A1 Apr. 21, 2022

(30) Foreign Application Priority Data

Jan. 17, 2019 (DE) .................. 10 2019 101 238.4

(51) Int. Cl.
*D04C 1/06* (2006.01)
*D04C 3/48* (2006.01)
(52) U.S. Cl.
CPC ................. *D04C 1/06* (2013.01); *D04C 3/48* (2013.01); *D10B 2509/06* (2013.01)

(58) Field of Classification Search
CPC ......... D04C 1/06; D04C 3/48; D10B 2509/06
(Continued)

(56) References Cited

U.S. PATENT DOCUMENTS 3,638,987 A * 2/1972 Fidrych .................. F16G 11/00
24/115 N
4,893,543 A * 1/1990 Phillips ..................... D04C 7/00
87/9

(Continued)

FOREIGN PATENT DOCUMENTS

DE 102014016832 B3 1/2016
DE 102015214699 A1 2/2017
(Continued)

OTHER PUBLICATIONS https://www.youtube.com/watch?v=2681yeSrsM0 (Year: 2016).*
(Continued)

*Primary Examiner* — Bao-Thieu L Nguyen
(74) *Attorney, Agent, or Firm* — Panitch Schwarze Belisario & Nadel LLP (57) ABSTRACT

A method for producing a single-filament stent from a filament having a first end and a second free end, wherein starting from the first end, a filament is wound onto a braiding core with a longitudinal axis in a spiral manner in the form of windings between a first deflection means in a proximal end region and a second deflection means in a distal end region, the filament is placed in a crossed-over position at a crossing point and introduced into a crossed-under position at another crossing point. The method also includes placing a winding onto the braiding core until reaching a crossing point, introducing and pushing the second free end of the filament in an insertion direction through a guide opening in the braiding core, arranged substantially perpendicular to the longitudinal axis, and
(Continued)

receiving and pulling the filament through the guide opening.

27 Claims, 4 Drawing Sheets

(58) Field of Classification Search
USPC .......................................................... 87/34
See application file for complete search history.

(56) References Cited

U.S. PATENT DOCUMENTS

| | | | | |
|---|---|---|---|---|
| 5,398,586 | A * | 3/1995 | Akiyama | D04C 1/06 87/6 |
| 5,939,216 | A * | 8/1999 | Kameda | D04C 1/06 428/323 |
| 6,241,757 | B1 * | 6/2001 | An | D04G 1/06 623/1.1 |
| 8,151,682 | B2 * | 4/2012 | Lilburn | D04C 3/48 87/9 |
| 8,333,222 | B2 * | 12/2012 | Leppla | D03D 35/00 139/192 |
| 8,459,164 | B2 * | 6/2013 | Lilburn | A61F 2/90 87/34 |
| 9,011,521 | B2 * | 4/2015 | Haug | A61F 2/2418 623/2.11 |
| 10,226,335 | B2 * | 3/2019 | Cartledge | A61F 2/2418 |
| 10,617,421 | B2 * | 4/2020 | Han | A61B 17/11 |
| 11,603,609 | B2 * | 3/2023 | Manz | D04C 3/06 |
| 11,707,368 | B2 * | 7/2023 | Folan | A61F 2/885 623/1.12 |
| 2005/0283962 | A1 * | 12/2005 | Boudjemline | D04C 1/06 29/433 |
| 2009/0157158 | A1 * | 6/2009 | Ondracek | A61F 2/90 623/1.2 |
| 2009/0198315 | A1 * | 8/2009 | Boudjemline | D04C 3/48 623/1.2 |
| 2010/0191319 | A1 * | 7/2010 | Lilburn | A61F 2/90 87/8 |
| 2011/0265908 | A1 * | 11/2011 | Clerc | D04C 7/00 29/559 |
| 2012/0330409 | A1 * | 12/2012 | Haug | A61F 2/2415 623/2.19 |
| 2016/0213498 | A1 * | 7/2016 | Wang | A61F 2/90 |
| 2020/0138609 | A1 * | 5/2020 | Rangwala | A61F 2/95 |

FOREIGN PATENT DOCUMENTS

| | | |
|---|---|---|
| DE | 102016102503 A1 | 8/2017 |
| EP | 1849440 A1 | 10/2007 |
| WO | 2010085794 A2 | 7/2010 |
| WO | 2011137043 A1 | 11/2011 |
| WO | 2013019851 A1 | 2/2013 |
| WO | 2017137577 A1 | 8/2017 |

OTHER PUBLICATIONS

Office Action issued Oct. 29, 2019 in DE Application No. 10 2019 101 238.4.

Int'l Search Report issued May 8, 2020 in Int'l Application No. PCT/EP2020/051172.

Kathrin Kurtenbach, Verfahrensauswahl zur Herstellung metallischer Atemwegstents (Process Selection for the Production of Metallic Airway Stents), pp. 126 and 196, PHD-thesis, Univ.-Prof. Professor h.c. (MGU) Dr.-ING. Dipl.-Wirt. Ing Thomas Gries, Anchen, Germany, Mar. 2017.

* cited by examiner

METHOD FOR PRODUCING A BRAIDED SINGLE-FILAMENT STENT, DEVICE AND BRAIDING CORE FOR THIS PURPOSE, AND BRAIDED SINGLE-FILAMENT STENT

CROSS-REFERENCE TO RELATED APPLICATIONS

This application is a Section 371 of International Application No. PCT/EP2020/051172, filed Jan. 17, 2020, which was published in the German language on Jul. 23, 2020 under International Publication No. WO 2020/148444 A1, which claims priority under 35 U.S.C. § 119(b) to German Application No. 10 2019 101 238.4, filed on Jan. 17, 2019, the disclosures of which are incorporated herein by reference in their entireties.

BACKGROUND OF THE INVENTION

The present invention relates to a method for producing a braided single-filament stent with the features of claim 1, a braided single-filament stent with the features of claim 14, a braiding core, particularly a braiding core for implementing the method with the features of claim 15, and a device for implementing the method for producing a braided single-filament stent with the features of claim 23.

Stents in various embodiments are known from prior art and are used preferably in hollow organs and vessels. A stent is a tubular endoprosthesis, which can be preferably implanted in a minimally invasive fashion in the hollow organ or vessel in order to stabilize a lumen inside the hollow organ or vessel, and maintain the functionality of said hollow organ. Here, hollow organs include for example the respiratory tract, the digestive tract, as well as urinary and biliary tracts, as well as the cardiovascular system, and here the application in the above-mentioned organs has been proven to be particularly beneficial.

A plurality of methods for producing stents is known from prior art. These production methods include the 2D-braiding technique, the 3D-braiding technique, the winding technique, as well as manual braiding methods, whereas the respectively applied production method is of essential influence upon the later features of the stent generated.

The automatic braiding technology is here characterized in the fact that a plurality of filaments can simultaneously be applied on a core and the filaments are connected to each other at their crossing points, particularly at the end of the stent, in order to prevent any disintegration of said stent. Due to complete automation being possible of the 2D-braiding technique and the 3D-braiding technique these fast and cost-effective methods have proven successful for the production of cylindrical stents and dog-bone shaped stents, however they are problematic at the ends of the stents. At the end side of the stents the filaments must be connected to each other by way of welding processes, which results in the end sections of the stent being subjected to traumatic stress of the adjacent braid, so that here expensive post-processing is required for precautionary reasons. Furthermore it has shown that the stents in the respective hollow organ are subjected to dynamic stress and the welded connections experience constant cyclical stress, so that here the risk is given that after several thousand cycles the welded connections may break. This leads then to a reduced stabilizing effect of the stent and may require additional surgeries of the patient.

Braided stents are typically single-filament stents, which are placed onto a braiding core in a usually manual process, as known for example from DE 10 2016 102 503 A1 or WO 2017/137 577 A1. The braiding core is typically a cylindrical core with a proximal end section and a distal end section, distanced therefrom, with deflecting pins being arranged in the respective proximal end section and the respective distal end section. The single-filament stent is produced from a filament showing a first end and a second end, preferably comprising a titanium-nickel alloy, particularly nitinol. Starting at the first end, the filament is placed in a spiral manner in windings from the proximal end section to the distal end section and via the deflection pins back to the proximal end section in a repeated fashion, while in crossing points, i.e. the points in which two windings intersect at an angle to each other, the respectively placed winding being placed upon the respectively earlier placed winding, thus forming the so-called crossed-over formation. In order to provide the braided single-filament stent with sufficient stability and to prevent any fraying of the braided single-filament stent, the two placed windings are welded to each other in a plurality of crossing points. In such single-filament stents it has also proven disadvantageous that the welding sites have negative consequences upon the quality and life span of the stents, and that additionally the stabilizing effect of such stents upon the hollow organ decreases.

Manually braided single-filament stents are produced in an expensive production method by braiding onto a braiding core. Such stents are custom made. Here, a braiding core is used for the manual braiding process, which is formed similar to the above-mentioned braiding core, however shows a plurality of guide openings, which are implemented in the braiding core in a spiral or helical fashion. Unlike the braided single-filament stents, at the crossing points here the windings are placed alternatingly in a crossed-over formation over a previously placed winding and introduced in a crossed-under formation underneath a previously placed winding, thus forming a web. Only the two ends of the filament are connected to each other by way of a weld. A scientific study "Verfahrensauswahl zur Herstellung metallischer Atemwegstents" (Selection of method for producing metallic respiratory stents), Kathrin Kurtenbach, 2016, has compared the above-mentioned methods and concluded that manually braided single-filament stents are far superior to other stents, since in particular here a maximum of geometric plurality and a particularly flexible stent structure can be realized with non-traumatized ends of the stents. Manually braided single-filament stents are free from any welding points, which stabilize the structure, so that such stents show a particularly long life span, which contributes to the safety of the patient.

However, in this method it has proven particularly disadvantageous that the production of manually braided single-filament stents requires highly qualified personnel, which must be capable to produce the stents in consistent quality. In particular, upholding a constant filament tensions, the insertion of the filament into the guide openings in the braiding core requires a maximum of concentration and experience, resulting in the production of such manually braided single-filament stents being subject to considerable expenses. Furthermore it has proven disadvantageous that during the insertion and pulling of the filament through the guide openings the filament may be partially twisted and the surface of the filament being compromised by contacting the guide openings, which may lead to negative consequences upon the longevity of the stent.

BRIEF SUMMARY OF THE INVENTION

The object of the present invention is to provide a method for producing a single-filament stent, which allows in a beneficial fashion the automated production of a braided single-filament stent without showing the disadvantages of those known from prior art. The production method shall particularly provide a completely or partially automated process in order to replace labor-intensive processing steps with a suitable production method for generating a consistent and higher quality product with lower or negligibly low rejects. Furthermore, a braiding core as well as a device for implementing the method shall be presented which allow a fully automated process.

These objectives are attained according to the invention in a method for producing a braided single-filament stent with the features of claim 1, a braiding core with the features of claim 15, and in a device for implementing the method according to the invention with the features of claim 23. Furthermore, the objective is attained in a braided single-filament stent with the features of claim 14.

For implementing the method according to the invention with the features of claim 1 a filament is provided with a first end and a second end as well as a braiding core, with the braiding core comprising a proximal end section and a distal end section arranged distanced from the proximal end in the longitudinal axis. In the proximal end section at least one first deflection is arranged and at least a second deflection in the distal end section. The braiding core comprises at least one guide opening between the proximal end section and the distal end section, integrated or inserted essentially perpendicular in reference to the longitudinal axis. Starting from the first end the filament is placed onto the braiding core in a spiral or helical fashion in windings between at least a first deflection and at least a second deflection, with the filament being placed at least at one crossing point over an already placed winding in a crossed-over formation, and the filament is inserted at least at one crossing point under an already placed winding, with the method according to the invention being characterized in the following processing steps to form such a crossed-under formation:

placing a winding onto the braiding core until a crossing point is reached, inserting and guiding the second end of the filament in a direction of insertion through the guide opening in the braiding core, and receiving and pulling the filament through the guide opening.

According to the invention the acknowledgement is essential that during the insertion of the filament, in order to form a crossed-under formation, the free end of the filament is not guided along the spiral or helical winding, but is essentially perpendicular to the longitudinal axis of the braiding core, considerably facilitating the insertion, the receiving, and the pulling through of the filament. The guide opening, essentially arranged perpendicular to the longitudinal axis, allows the arrangement of the free end of the filament along a direction of insertion along a straight line, arranged like a secant in reference to the braiding core, guided through the guide opening, whereas the braiding cores known from prior art require that the free end of the filament is inserted along a bent (helical) curve through the guide opening. In the context of the present invention an alignment that is essentially perpendicular shows an angular tolerance of ±15°, preferably ±10°, further preferred ±5°, even further preferred ±2.5°, and particularly preferred ±1°. The term like a secant may be understood in the context of the present invention as an arrangement of a straight line in the form of a secant which intersects in two points the jacket of the braiding core and is distanced from a center and the longitudinal axis, respectively.

According to another advantageous embodiment of the present method according to the invention it is provided that the filament is pulled through the guide opening until the windings of the filament are placed on the braiding core with a predetermined and preferably constant tension. By pulling the filament, here the filament is preferably positioned on the braiding core such that it contacts said core at its final position in the winding. Due to the tightening the filament is not contacting the base of the guide opening but bridges and/or spans over the guide opening, due to tensile stress, allowing to realize the final positioning on the braiding core.

Another advantageous embodiment of the present invention provides that the direction of insertion is aligned parallel in reference to the guide opening. It is further preferred for the free end of the filament to be inserted and pulled through in the direction of insertion in a centered fashion in reference to the guide opening. This allows to realize a guiding of the filament in the guide opening free from any contacting, to the extent possible, preventing any damages of the filament due to contact friction at the guide opening of the braiding core, According to another advantageous embodiment of the method according to the invention a first gripper holds the filament at a distance from the free end and inserts the free end in the direction of insertion into the guide opening in order to form a crossed-under formation. Here, the distance of the free end from the first gripper is at least equivalent to the length of the guide opening (in the direction of insertion) and/or measures at least one third of the diameter of the braiding core. It is preferred that the distance exceeds the diameter of the braiding core. The first gripper may be addressed by CNC (computer numeric control) and mobile in reference to the braiding core, allowing a precise positioning of the free end in reference to the respective guide opening. Here the first gripper holds the filament such that it is fixed in its position and when controlled by the gripper no change of position of the filament can occur, e.g., any undesired shifting or twisting. Once the filament has been inserted the first gripper can release the filament and reengage and/or receive the filament again at the side behind the guide opening, when seen in the direction of insertion.

Furthermore it is particularly advantageous for the first gripper or any second gripper to be provided and implemented for accepting the free end of the filament behind the guide opening, when seen in the direction of insertion. The second gripper may include the first gripper.

Furthermore, the second gripper may be embodied like the first gripper and guided by CNC, allowing a precise positioning in reference to the braiding core for receiving the free end of the filament, inserted through the guide opening, on the side of the guide opening located opposite the first gripper.

When implementing the method according to the invention it is particularly advantageous for the first gripper to hold the filament at least until the time when the second gripper also holds the free end of the filament. As soon as the second gripper has accepted the free end of the filament and holds it, the first gripper can release the filament. This way it is ensured that the control of the filament remains uninterrupted during the implementation of the method according to the invention and for example any undesired twisting of the filament is prevented.

Another advantageous version of the method according to the invention provides that the filament is being pulled, starting with the free end, by way of winding about a second axis onto a bobbin. It is preferred for at least one of the grippers, preferably the second gripper, which receives the free end behind the guide opening, rotates together with the bobbin about the second axis in order to pull through and wind the filament through the guide opening, causing the filament, during the winding process, to be completely controlled during the placement of the filament. Furthermore it is particularly preferred if initially the second gripper pulls the free end of the filament in the direction of insertion through the guide opening and the first gripper follows the actuating motion of the second gripper and also reengages and holds the filament behind the guide opening, seen in the direction of insertion. Subsequently the first gripper, together with the second gripper and the bobbin, can be rotated about the second axis for completely pulling the filament through the guide opening and winding the filament.

It is particularly preferred when during the winding of the filament onto the bobbin or during the placement of the filament onto the braiding core the specified tension of the filament on the braiding core is being monitored, for example by at least one force sensor and/or torque sensor, which detects at the filament the torque and/or tension and/or tensile force applied upon the bobbin.

A particularly preferred embodiment of the present invention provides that the first axis is aligned either parallel in reference to the longitudinal axis of the braiding core or that the second axis is aligned perpendicular to the longitudinal axis of the braiding core.

When implementing the method according to the invention it may also be advantageous for the filament, after being pulled through the guide opening, to be held for the formation of a crossed-under formation on the braiding core. It is particularly preferred when at least one holding means is provided that is implemented such that a retention force is applied upon the winding of the filament. Said holding means may fix at least one winding placed upon the braiding core and fixate the winding until the next crossed-under formation is reached.

It has furthermore proven to be advantageous when the filament, before the insertion and piercing of the free end of the filament to form a crossed-under formation, is completely wound off the bobbin. After the unwinding from the bobbin, the free end of the filament is positioned in the direction of insertion in front of the next guide opening in order to form another crossed-under formation. For this purpose preferably the braiding core may be twisted in the longitudinal axis and an equivalent lateral motion be performed along the longitudinal axis between the proximal end section and the distal end section of the braiding core in order to position, according to the pitch of the winding, the free end of the filament in front of the respective guide opening.

Furthermore it is advantageous when a guiding device is arranged at the second end of the filament, which shows greater stiffness than the filament. The guiding device may guide the filament in the manner of a needle and thread—principle, for example, allowing the first gripper and the second gripper not to hold the filament but instead the guiding device, which considerably facilitates the handling of the filament when implementing the method according to the invention. It is particularly preferred when the shape of the guiding device is adjusted to the shape of the guide opening. The guiding device and the guide opening may for example show a polygonal cross-section. This way, when positioned in the guide opening the guiding device cannot be rotated in the guide opening due to the positive fit (with play), preventing any undesired distortion of the filament when generating a crossed-under formation. The guiding device can be fastened at the filament when providing said filament.

Another advantageous embodiment of the present invention provides that the first end and the second end of the filament are connected to each other in a joint winding. A weld is particularly preferred arranged centrally between the proximal end section and the distal end section. It is even more preferred when the weld is arranged in a crossed-under formation. The weld can preferably be generated via electric beam welding, laser welding, resistance welding, friction welding, or micro-plasma welding. After the welding process, the free end sections of the first end and the second end of the filament can be severed beyond the weld. Then, on the one side the weld is located in an area with low mechanic stress and on the other side the weld is positioned without generating any trauma.

It has proven particularly advantageous for the placed filament to be pulled out of the respective guide opening and to bridge and/or span over the guide opening due to the filament tension. This way, the guide opening is released and the filament can be repeatedly inserted, along the windings according to the above-described method, through at least one guide opening in order to form a crossed-under formation. In this winding then at least two sections of the filament are located directly side-by-side. In particular, the connection of the first end and the second end of the filament in a common winding with two sections is considerably facilitated. Additionally, the sections can be twisted with each other in one or more windings. Furthermore it is advantageous when the braided single-filament stent after the braiding process is post-processed by way of tempering and/or electro-polishing. It is preferred that the processing step of tempering is performed before the single-filament stent is removed from the braiding core. It is further advantageous for the single-filament stent to be electro-polished after the removal from the braiding core, allowing even minute surface damages, particularly scratches, to be removed. This increases the lasting stability of the braided single-filament stent.

It has furthermore proven advantageous when for the production of the braided single-filament stent a metallic filament is used or one produced from a polymer. The filament may particularly preferred represent a single filament. Alternatively the filament may represent a filament produced from several individual filaments (laces), with it being possible to produce the laces from different materials. It is preferred to use for the filaments the following materials or material groups: nickel-titanium alloys, particularly nitinol, magnesium alloys, stainless steel, particularly medical-grade stainless steel (e.g., 316LVM), chromium alloys, cobalt-chromium alloys, cobalt alloys, niobium comprising alloys, platinum alloys, platinum-chromium alloys, tantalum alloys. It is also possible to use a filament produced from a polymer or polymer mixture for the production of a braided single-filament stent.

It is advantageous when for the production of a single-filament stent a filament is used with a diameter ranging from 1 µm to 1000 µm, preferably in the case of a blood-vessel single-filament stent ranging from 10 µm to 350 µm, and preferably in the case of a pulmonary, tracheal, laryngeal, ureteral, gastro-intestinal, or biliary tract—single-filament stent ranging from 10 µm to 500 µm.

Preferably the helical windings are placed such onto the braiding core wing an intersecting angle $\alpha$, in which the two braids cross and/or intersect at a crossing point, ranging $10° \leq \alpha \leq 80°$, preferably ranging $30° \leq \alpha \leq 60°$.

A second and additional aspect of the present invention relates to a single-filament stent produced with a method according to the invention.

A third aspect of the present invention relates to a braiding core, particularly a braiding core for implementing the method according to the invention, comprising a core with a longitudinal axis, a proximal end section, and a distal end section, with the proximal end section being arranged at a distance from the distal end section in the longitudinal axis. Furthermore the braiding core comprises at least a first deflection and at least a second deflection, with at least a first deflection being arranged in the proximal end section and at least a second deflection being arranged in the distal end section. According to the invention at least one guide opening is arranged between the proximal end section and the distal end section, which opening is essentially arranged perpendicular in reference to the longitudinal axis. In the context with this invention, here an arrangement is understood that is aligned essentially perpendicular to the longitudinal axis as one with an angular tolerance of ±15°, preferably less than ±10°, further preferred less than ±5°, even further preferred less than ±2.5°, and most preferred less than ±1° between the alignment of at least one guide opening and the longitudinal axis. The guide opening is integrated or formed in the core and may be embodied like a secant or as a groove aligned perpendicular to the longitudinal axis. The depth and width of the guide opening is adjusted to the size of the filament and shows at least the same size as the filament to be guided through the guide opening. The width of the guide opening is limited by the mesh width, with the mesh width describing the distance between the crossing points parallel in reference to the longitudinal axis.

According to another advantageous embodiment of the present invention the core is embodied in a cylindrical fashion. In particular it is preferred when the core between the proximal end section and the distal end section shows a constant diameter or when the core between the proximal end section and the distal end section shows an initially tapering and then again enlarging diameter, allowing to create a braided single-filament stent with a dog-bone shape.

According to another advantageous embodiment of the present invention at least one deflection is embodied by a deflection pin projecting from the core, preferably in a radial fashion. The deflection pins may be fastened at the core of the braiding core in a detachable fashion, so that for the removal of the braided single-filament stent the deflection pins in the proximal end section and in the distal end section can be removed and the single-filament stent can be pulled off or removed from the braiding core. The deflection pins may be embodied as clamps, arches, T-shaped pins, or the like.

Furthermore it has proven advantageous when in the proximal end section and in the distal end section respectively a plurality i of deflection means am arranged. It is particularly preferred for the deflection means to be arranged in the proximal end section and in the distal end section in a fashion symmetrical in the circumferential direction. The quantity i of deflection means in the proximal end section and in the distal end section may preferably represent an even number. A particularly preferred embodiment of the braiding core provides however that in the proximal end section and in the distal end section respectively ten or twelve deflection means (i=10 or i=12) are arranged in a manner symmetrical in the circumferential direction.

It is advantageous when at least one guide opening is a recess, circling the core perpendicularly in reference to the longitudinal axis and/or when at least one guide opening is a recess integrated or formed in the core in the manner of a secant.

An opening may be formed in a particularly simple and cost-effective fashion by an appropriately cutting production process, e.g., drilling into the core, or when originally forming or deforming the core into its shape.

It may also be advantageous for the guide opening to be a recess formed in the core in the form of a secant, thus representing a recess aligned in a tangential direction. The respective recess may be formed into the core or integrated therein.

It is preferred that a plurality j of guide openings is embodied over the circumference of the core in a level perpendicular to the longitudinal axis. The guide openings may be embodied at a distance from each other, whereas any windings placed between the guide openings not being influenced. Furthermore it is advantageous when a plurality k of guide openings is arranged in rows along the longitudinal axis.

It is advantageous when at least one guide opening shows in the cross-section a rectangular, a U-shaped or V-shaped cross-section, or a combination thereof. In particular, it has proven advantageous when the guide opening shows a variable width. It is particularly preferred when the width of the guide opening increases, starting at a central point of the guide opening, further preferred in both directions, which facilitates the threading and the insertion of the free end of the filament and further allows reducing the positioning expense during the insertion and penetration of the free end of the filament.

A fourth aspect of the present invention relates to a device for implementing the method according to the invention to produce a braided single-filament stent. The device for implementing the method comprises a first axis and a second axis, with the first axis being implemented to hold and/or receive a braiding or winding core, particularly a braiding core according to the invention. Furthermore the invention comprises at least one arm with at least one gripper, with at least one gripper being implemented to engage the filament and to hold it. At least one arm and at least one bobbin are arranged in a manner rotational about the second axis. It is provided according to the invention that the braiding core is held in a manner rotational about the first axis, with the device preferably controlling the rotation of the braiding core about the first axis. Furthermore the device controls the second axis such that the bobbin and the arm are rotated jointly in the second axis. During one rotation about the second axis the arm and/or at least one gripper thereof can hold the free end of the filament, while simultaneously the filament is wound onto the bobbin or unwound from the bobbin.

According to another advantageous embodiment of the present invention at least one arm comprises the first gripper and a second gripper, arranged at a distance from each other and jointly rotational about the second axis. The first gripper and the second gripper my each be addressed separately by a control means of the device such that the first gripper and/or the second gripper each can perform independently a motion for receiving, grasping, and holding the filament.

According to an advantageous embodiment of the device according to the invention for the production of a braided single-filament stent the first axis and/or the second axis show at least one force sensor, which is embodied to determine the torque and/or lateral force applied to the first axis and/or the second axis. Based on the determination of the torque applied to the first axis and/or the second axis and/or the lateral force applied to the first axis and/or the second axis, here the tensile force can be determined, which pulls the filament during the placement upon the braiding core, which allows to ensure that the filament, when being placed upon the braiding core, is placed with a constant and predetermined tension.

According to another embodiment of the present invention it may be advantageous that at least one arm is mobile in reference to the first axis. Preferably at least one arm is controlled by the control means of the device using CNC, allowing at least one gripper to be respectively positioned precisely. This is necessary, for example, in order to position the gripper on the one side in a direction of insertion in front of the braiding core and the guide opening and on the other side to receive the free end of the filament in the direction of insertion behind the braiding core. While the first gripper is preferably embodied to guide a free end of the filament, projecting from the gripper, to form a crossed-under formation in a crossing point, the second gripper is preferably embodied to receive the filament and/or its free end after the formation of the crossed-under formation and to pull it through said crossed-under formation. In a particularly preferred embodiment of the present invention, after the formation of the crossed-under formation the first gripper and the second gripper can jointly hold the filament and can be rotated together with the bobbin about the second axis, resulting in the filament, during the winding about the bobbin, to be secured from changing its position and it can be prevented that the filament is twisted.

It is preferred for the first axis and the second axis to be aligned parallel in reference to each other or for the first axis and the second axis to be aligned perpendicular to each other.

Furthermore it is provided, according to one feature of the present invention, that the device comprises at least one holding means, which is implemented to apply a holding force upon the braiding core. It is particularly preferred that the holding means allows to fix a winding, placed on the braiding core, on said braiding core such that the tension of the filament of the already placed windings on the braiding core is not being lost. It is particularly preferred when at least one holding means is rotational about a first axis, with it furthermore being particularly preferred when at last one holding means can be rotated about the first axis together with the first axis and/or with a braiding core arranged in the first axis.

BRIEF DESCRIPTION OF THE SEVERAL VIEWS OF THE DRAWING

The foregoing summary, as well as the following detailed description of the preferred invention, will be better understood when read in conjunction with the appended drawings. For the purpose of illustrating the preferred invention, there are shown in the drawings embodiments which are presently preferred. It should be understood, however, that the invention is not limited to the precise arrangements and instrumentalities shown. In the drawings.

Here, identical reference characters refer to identical or similar parts even in different illustrations. For better visibility, not all reference characters are displayed in all figures.

DETAILED DESCRIPTION OF THE INVENTION

Figure 1:
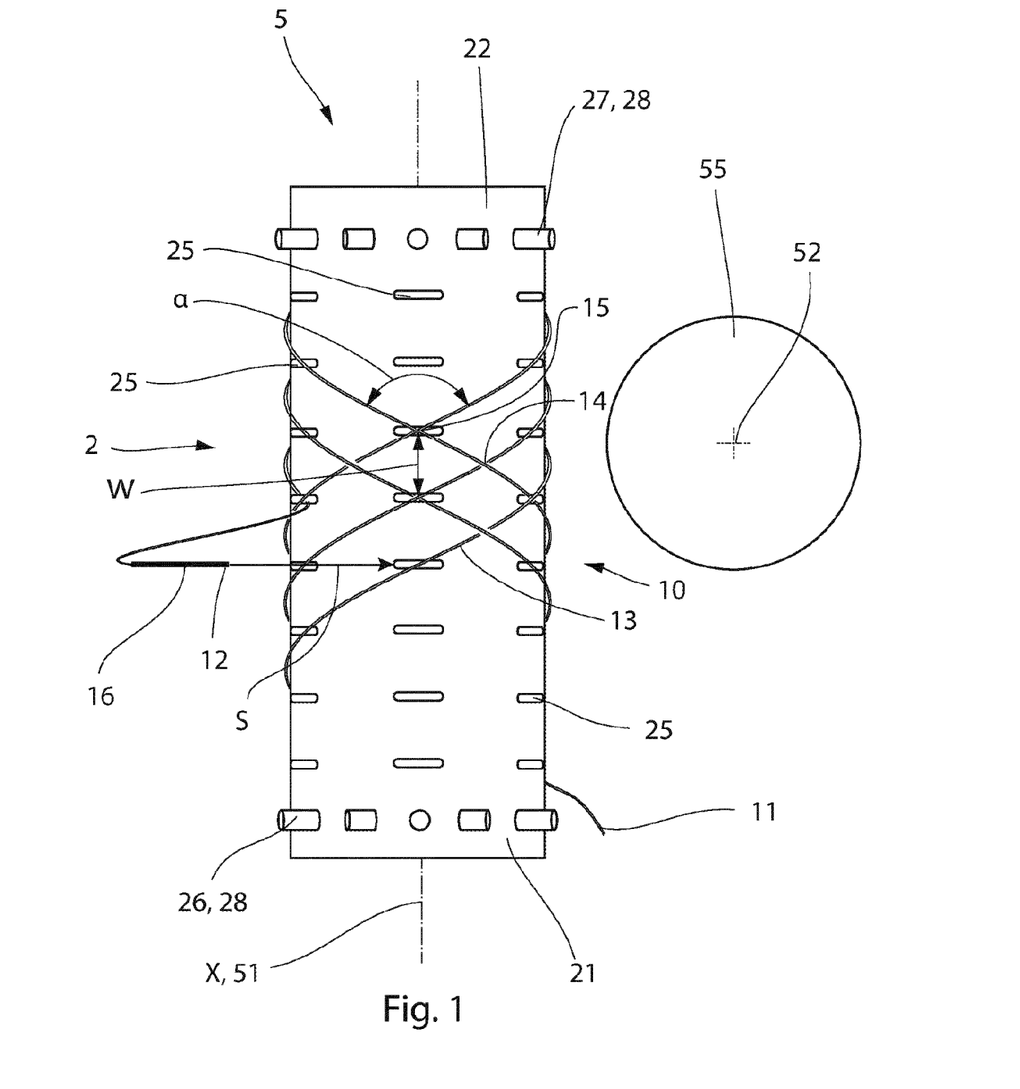
FIG. 1 is a largely simplified top perspective illustration of a device according to the invention for producing a braided single-filament stent with a braiding core, with the braiding core comprising a plurality of guide openings, which are embodied for the formation of a crossed-under formation in a crossing point perpendicular in the braiding core.

FIG. 1 shows the device 5 for the production of a braided single-filament stent comprising a filament 10. The device 5 comprises a first axis 51 and a second axis 52, which in the exemplary embodiment shown are aligned perpendicular in reference to each other, but which may also be aligned parallel to each other. The first axis 51 and the second axis 52 may represent machine axles and may each be independently addressed by a control means of the device 5.

For the production of a braided single-filament stent a braiding core 2 is coupled with the device 5 in a first axis 51, resulting in the braiding core 2 being coupled in the device 1 to the respective machine axle of the device in a driving fashion and is held rotationally about the first axis 51.

In the second axis 52 an arm 54, see FIGS. 2a to 2g, and a bobbin 55 are held rotationally, with the second axis 52 being mobile in reference to the first axis 51. The arm 54 comprises a first gripper 61 and a second gripper 62, which independently from each other can be addressed by the control means of the device and are implemented to engage the filament 10 and to hold it. With the arm 54 the grippers 61, 62 can be positioned in reference to each other and with the arm 54 jointly in reference to the first axis 51.

The braiding core 2 comprises a cylindrical core 20 with a longitudinal axis X, a proximal end section 21, and a distal end section 22. The proximal end section 21 and the distal side 22 are arranged parallel and at a distance in the longitudinal axis X. The proximal end section 21 comprises a plurality of first deflections 26 and the distal end section 22 shows a plurality of second deflections 27, with the respective deflections 26, 27 being embodied as a deflection pin 28 projecting from the jacket of the cylindrical core 20. The respective deflection pin 28 may represent a clamp, an arch, a flange, or a T-shaped pin.

In the exemplary embodiment shown, both in the proximal end section 21 as well as in the distal end section 22 respectively a plurality i of twelve deflection pins 28 is arranged on the jacket, symmetrical in the circumferential direction, with the deflection pins 28 being fastened in a detachable fashion at the cylindrical core 20. The number i can be selected arbitrarily and the number i of the first deflections 26 and the second deflections 27 shall be identical, with here preferably the number i representing an even number. The deflection pins 28 are embodied preferably in a cylindrical fashion and project preferably radially from the jacket of the core 20.

Furthermore it is shown in FIG. 1 that between the proximal end section 21 and the distal end section 22, between the first deflection 26 and the second deflection 27, a plurality of guide openings 25 is arranged in columns, which are aligned essentially perpendicular to the longitudinal axis X. The respective guide opening 25 is formed in the core 20 along a secant, with the secant by definition intersects the jacket of the preferably cylindrical core 20 at two points and accordingly is arranged between a tangent and the longitudinal axis X. In a level, respectively in a manner symmetrical to the circumference about the longitudinal axis X, a plurality j of guide openings 25 is arranged, perpendicular to the longitudinal axis, with the number j being equivalent to half the number i of deflections 26, 27, thus j=i/2.

The guide openings 25 are arranged in columns along the longitudinal axis X at a number of k, with the number k depending on a mesh width W and a distance between the proximal end section 21 and the distal end section 22, which is equivalent to a length of the single-filament stent to be braided.

The respective guide opening 25 can be embodied or implemented as a tangentially and/or secantially extending groove or recess, perpendicular to the longitudinal axis X, in the jacket of the core 20, or alternatively be embodied as a circumferential groove (not shown).

Figure 4:
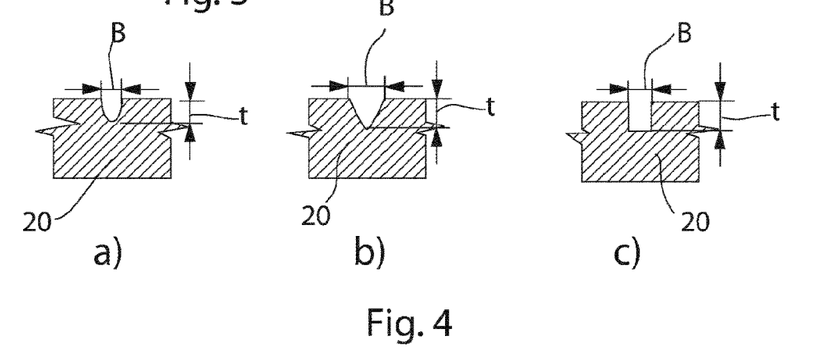
FIGS. 4a to 4c are comprised of schematic cross-sectional views wherein the cross-sections are taken through the guide opening.

The respective guide opening 25 shows a width B and a depth T and may show any arbitrary form in its cross-section, and here three typical cross-sections for a guide opening 25 are shown in the FIGS. 4a to 4c. In its cross-section the guide opening 25 may for example show a U-shaped cross-section, illustrated in FIG. 4a. The guide opening 25 may also show a V-shaped cross-section, see FIG. 4b, or a rectangular cross-section, see FIG. 4c. The width B and depth T of the guide opening 25 is adjusted to the size of the filament 10, which is used for the formation of the braided single-filament stent. The width B is at least of equal size as the diameter of the filament 10 used, with the maximum width B being limited by the mesh width W and thus preferably amounting to no more than 0.9*W.

Figure 3:
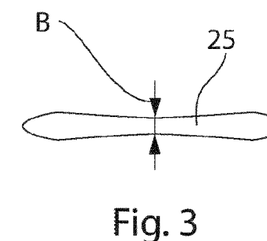
FIG. 3 is an enlarged side elevational view of a guide opening of one of the guide openings of the plurality of guide openings according to FIG. 1 or 2.

Furthermore it is discernible from FIG. 3 that there is no requirement for the width B of the guide opening 25 to be constant, but the width B may be embodied variable in the respective guide opening 25. It is preferred for the width B, starting from the center of the guide opening 25, to increase towards the ends of the guide opening 25, in which the guide opening 25 transfers to the jacket of the core 20.

For the formation of the braided single-filament core the filament 10 is placed upon the braiding core 2, with the filament 10 comprising a first end 11 and a second end 12. The filament 10 may be produced from a metallic material or a synthetic material, for example polymer fibers, and show a diameter from 1 µm to 1000 µm, depending on the intended use of the tubular braided single-filament stent.

It is particularly preferred for the filament 10 to be produced from a titanium-nickel alloy, for example nitinol, and showing a diameter of approx. 350 µm.

As explained in the following based on FIGS. 2a to 2g, starting at the first end 11 the filament 10 is placed onto the braiding core 2 in spiral or helical windings 13, with here perhaps a guiding device 16 being arranged at the second end 12 for better handling of the filament 10. The guiding device 16 may for example be coupled via a form-fitting, force-fitting, or material-to-material connection to the second end of the filament 10, with the guiding device 16 showing a higher stiffness than the filament 10. In particular, the guiding device 16 may also show a greater diameter, even a cross-section which is not rotary symmetrical, particularly a square cross-section, which improves the handling of the filament 10.

For this purpose the first end 11 is fastened at the braiding core 2 at the proximal end section 21 and, starting from the first end 11, placed with the free end 12 onto the braiding core 2 until a deflection pin 28 of the second deflections 27 is reached in the distal end section 22. Subsequently the filament 10 is placed about one of the deflection pins 28 and guided in another winding 13 spirally or helically about the core 20 to the first deflections 26 in the proximal end section 21. This process is repeated until the winding 13 crosses during the placement process an already placed winding 13 in a so-called crossing point, with in this crossing point either the free end 12 being placed in a crossed-over formation 14 upon the first winding 13 or guided or inserted in a crossed-under formation 15 underneath the first winding 13, forming a braid. The two windings 13 intersect in a crossing point at an intersecting angle α, which amounts, depending on a predetermined pitch of the braids 13, to approx. $10°≤α≤80°$ and preferably $30°≤α≤60°$.

The braid may be formed in any arbitrary sequence, with preferably the filament 10 being placed alternating at a crossing point in a crossed-over formation and inserted in a crossed-under formation 15. This yields particularly good mechanic features for the braided and tubular single-filament stent. Such braids can also be called plain bonds. Alternatively, braids with twill bonding are possible, atlas bonds (satin), or warp reinforced braids.

For the production of the single-filament stent the filament 10 is held at a distance from the second end 12 by at least one of the grippers 61, 62 and subsequently the filament 10 is wound onto the bobbin 55, starting at the second end 12. In order to place the filament 10 onto the braiding core 2, said braiding core 2 is rotated about the first axis 51, while the bobbin 55 unwinds the filament 10 under a constant filament tension in the second axis 52 accordingly and the bobbin 55 is displaced along the longitudinal axis X, causing the braid 13 to develop an appropriate pitch.

Figure 2A:
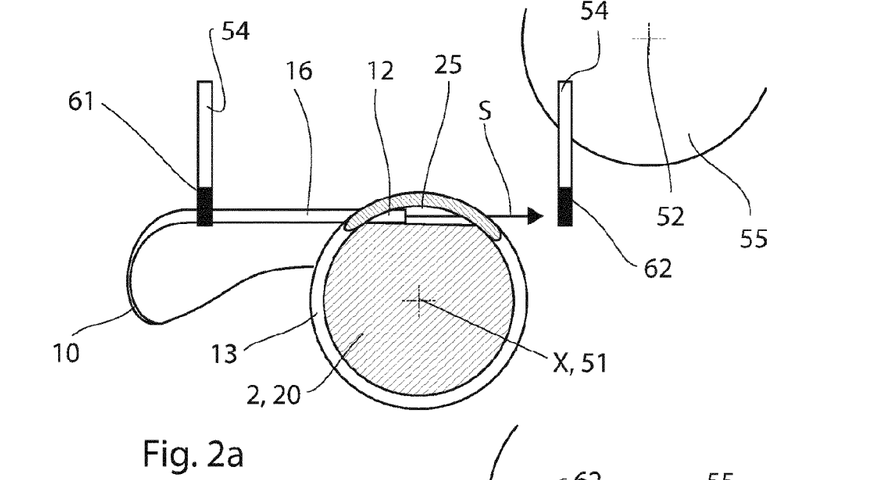
FIGS. 2a to 2g are side elevational, schematic and simplified illustrations of individual processing steps for the formation of a crossed-under formation with the device according to FIG. 1.
Figure 2B:
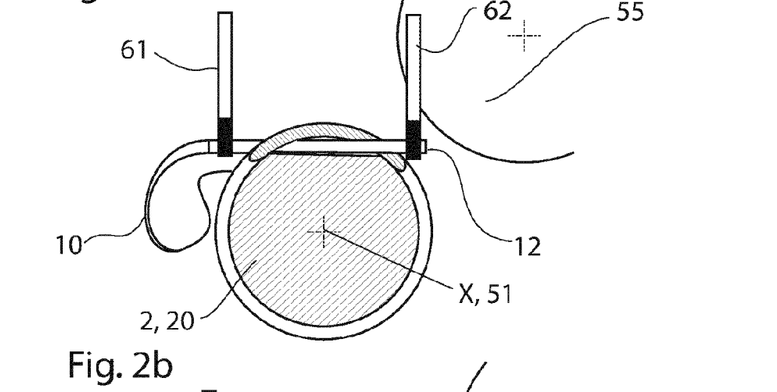
Figure 2C:
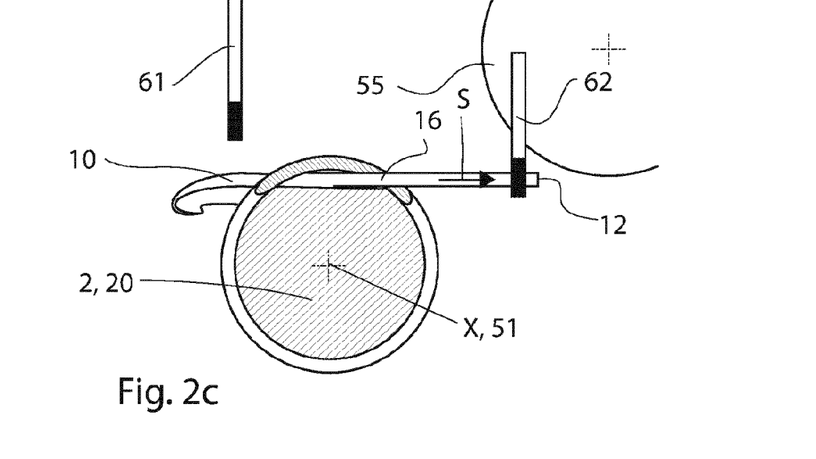
Figure 2D:
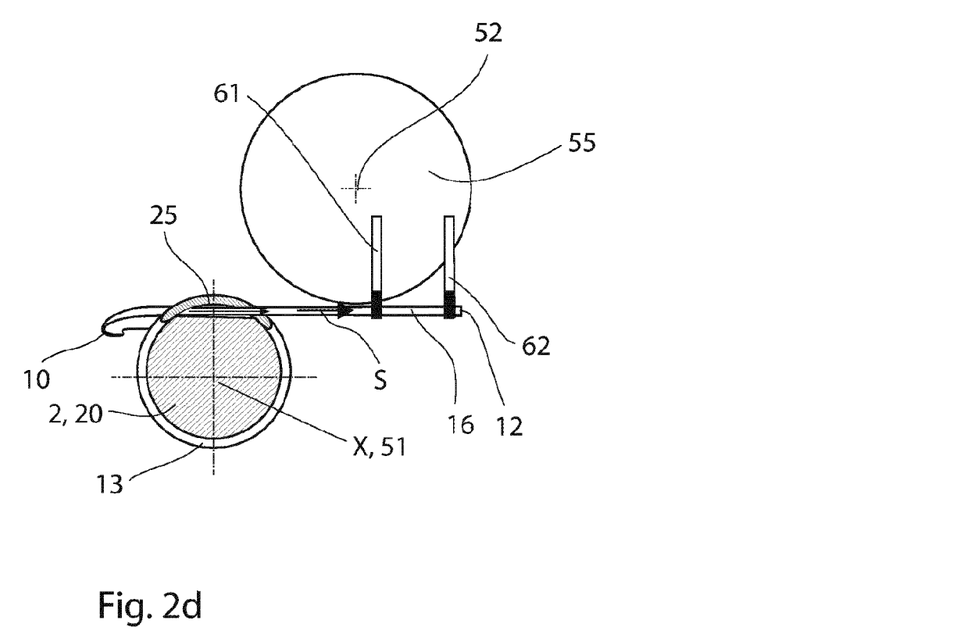
Figure 2E:
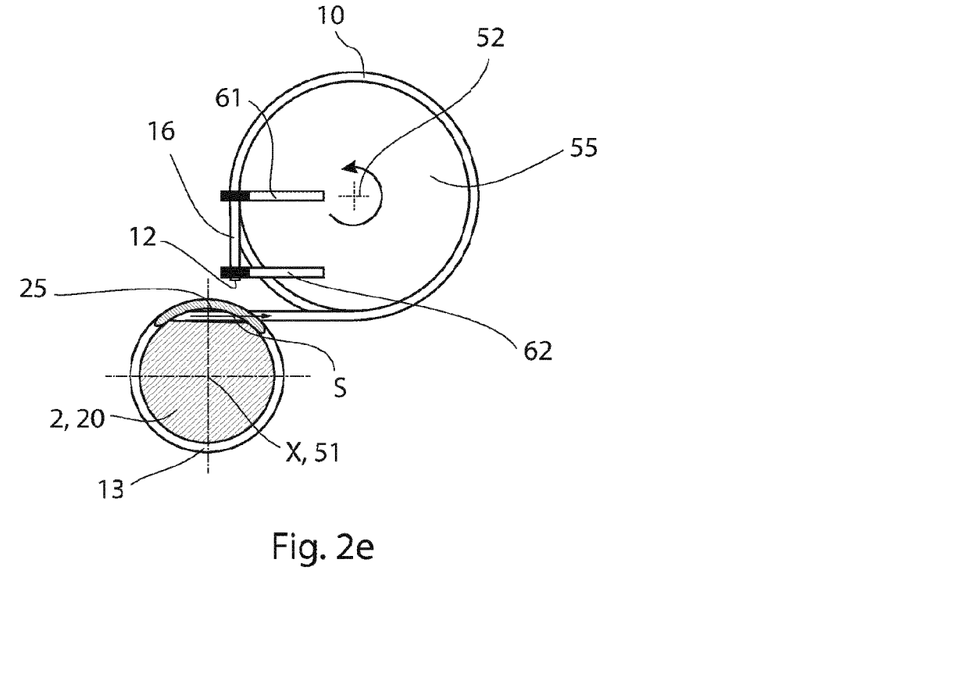
Figure 2F:
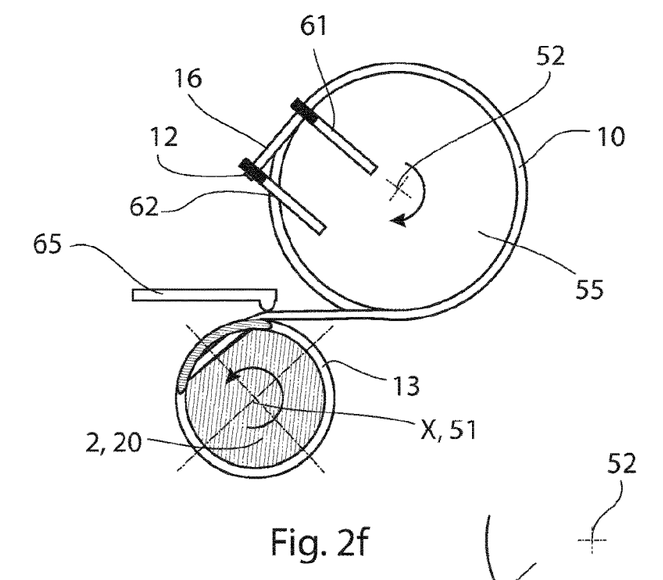
Figure 2G:
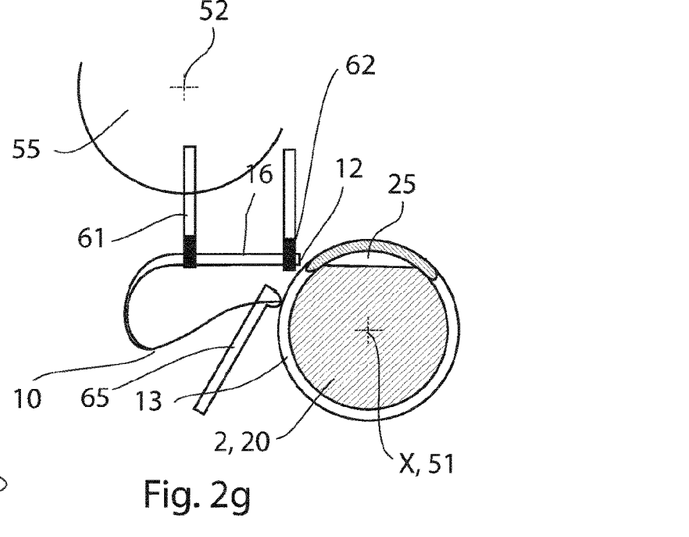

Upon reaching a crossing point in which a crossed-under formation 15 shall be created under an already placed first winding 13, said already placed winding 13 is fixated by a holding means 65. Subsequently the filament 10 is completely wound off the bobbin 55 and the first gripper 61 is positioned, seen in a direction of insertion S, in front of the respective guide opening 25, with the first gripper 61 positioning the filament 10 in the direction of insertion S coaxially in reference to the alignment of the guide opening. The second gripper 62, as shown in FIG. 2a, is positioned, seen in the direction of insertion S, behind the guide opening 25 for receiving the free end 12 of the filament 10, and subsequently the free end 12 of the filament 10 is inserted through the guide opening 25 and underneath the first winding 13 and received at the opposite side of the guide opening 25 by the second gripper 62. Only when the second gripper 62 has received the second end 12 of the filament and securely holds the free end 12 of the filament 10 then the first g ripper 61, as shown in FIG. 2c, releases the filament 10 so that the filament 10 can be pulled completely through the guide opening and the crossed-under formation 15. For this purpose initially the second gripper 62 can apply a tension upon the free end 12 of the filament 10 and subsequently, as shown in FIGS. 2d and 2e, the free end 12 of the filament 10 can be wound onto the bobbin 55 allowing the filament 10 to be pulled completely through the guide opening 25.

The first gripper 61 and/or the second gripper 62, as well as the first axis 51 and/or the second axis 52 may comprise force sensors (not shown), by which a tensile force applied at the filament 10 can be determined. It is particularly preferred when the force sensor can determine a torque applied at the bobbin 55 or the first axis 51.

After the filament 10 has been completely pulled through to form the crossed-under formation 15, the winding 13, as already described above, is placed further onto the braiding core 2, with the holding means 65 being positioned behind the crossed-under formation 15 and a holding force being applied thereby upon the winding 13 so that, for the generation of another crossed-under formation 153, during the unwinding of the bobbin 55*m* the tensile force of the filament 10 in the already placed winding 13 is not being lost. It is preferred that during the placement of the winding 13 the filament 10 is held under a predetermined and preferably constant tension.

The filament 10 is placed in windings 13 onto the braiding core 2 until the windings 13 placed are arranged parallel in reference to a first winding 13. These two windings 13 are preferably connected via a welded connection and subsequently the free end sections of the filament 10 located between the welded connection and the ends 11, 12 are severed and/or removed.

Subsequently the braiding core 2, together with the braided and tubular single-filament stent, can be removed from the device and post-processed in additional treatment steps. In a first additional processing step the single-filament stent on the braiding core 2 can preferably be post-processed thermally by way of tempering at approx. 500°.

Subsequently the deflection pins 28 can be released from the core 20 and the single-filament stent can be pulled off the core 20. In another processing step the surface of the filament 10 can be post-processed, for example by electropolishing.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

LIST OF REFERENCE CHARACTERS

2 Braiding core
5 Device
10 Filament
11 First end
12 Second end
13 Winding
14 Crossed-over formation
15 Crossed-under formation
16 Guiding device
20 Braiding core
21 Proximal end section
22 Distal end section
25 Guide opening
26 First deflection
27 Second deflection
28 Deflection pin
30 Guide opening
51 First axis
52 Second axis
54 Arm
55 Bobbin
61 First gripper
62 Second gripper
65 Holding means
B Width of 25

S Direction of insertion
T Depth of 25
X Longitudinal axis

The invention claimed is:

1. A method for the production of a single-filament stent comprising a filament with a first end and a second or free end, with the filament starting at the first end, being wound onto a braiding core with a longitudinal axis in a spiral fashion in the form of a winding between at least a first deflection in a proximal end section and at least a second deflection in a distal end section of the braiding core and the filament being placed at least in one crossing point in a crossed-over formation over the winding and at least another crossing point in a crossed-under formation under the winding, characterized in the processing steps for the formation of the crossed-under formation comprising:
   placing the winding onto the braiding core until the at least another crossing point is reached,
   inserting and pulling through the free end of the filament along a straight line arranged like a secant in reference to the braiding core in a direction of insertion essentially perpendicular to the longitudinal axis into a guide opening of the braiding core, and
   receiving and pulling the filament through the guide opening.

2. The method according to claim 1, wherein the filament is pulled through the guide opening until the winding of the filament is placed on the braiding core showing a predetermined tension.

3. The method according to claim 1, wherein the direction of insertion is aligned parallel in reference to the guide opening.

4. The method according to claim 1, wherein a first gripper holds the filament at a distance from the free end and the free end is inserted into the guide opening in the direction of insertion.

5. The method according to claim 4, wherein a second gripper receives the free end of the filament in the direction of insertion behind the guide opening.

6. The method according to claim 5, wherein the first gripper holds the filament at least until the second gripper holds the free end of the filament.

7. The method according to claim 1, wherein the filament is held on the braiding core after being pulled through the guide opening.

8. The method according to claim 1, wherein the pulling of the filament through the guide opening, starting from the second end, occurs by winding the filament onto a bobbin about a second axis.

9. The method according to claim 8, wherein after the winding of the free end of the filament onto the bobbin, said filament is placed onto the braiding core until a next crossing point is reached with a crossed-under formation.

10. The method according to claim 9, wherein the filament is placed onto the braiding core with a predetermined tension.

11. The method according to claim 8, wherein a complete unwinding of the filament from the bobbin occurs prior to the insertion of the free end of the filament in order to form the crossed-under formation.

12. The method according to claim 1, wherein a guiding device is arranged at the second end of the filament, which has greater rigidity than the filament.

13. The method according to claim 1, wherein the first end and the second end of the filament are connected to each other in a common winding.

14. A braiding core for the production of a single-filament stent with a filament, the braiding core comprising:
- a core with a longitudinal axis, a proximal end section and a distal end section,
- at least a first deflection and at least a second deflection, the at least first deflection positioned in the proximal end section and the at least second deflection positioned in the distal end section, the at least first and second deflections configured for winding the filament onto the core between the proximal and distal sections; and
- a guide opening being arranged between the proximal end section and the distal end section, which is formed in a manner of a secant groove and is arranged essentially perpendicular in reference to the longitudinal axis.

15. The braiding core according to claim 14, wherein the core is formed cylindrically.

16. The braiding core according to claim 14, wherein the respective first or second deflection is formed by a deflection pin projecting perpendicularly from the core.

17. The braiding core according to any of claim 14, wherein a plurality of deflections is respectively arranged at the proximal end section and the distal end section, with a quantity of the plurality of deflections being even.

18. The braiding core according to claim 14, wherein the guide opening is comprised of a recess, the recess circles the core in a perpendicular fashion in reference to the longitudinal axis.

19. The braiding core according to claim 14, wherein the guide opening is a recess in the core aligned tangentially.

20. The braiding core according to claim 14, wherein the guide opening has a rectangular cross-section, a triangular cross-section, or a rounded cross-section.

21. The braiding core according to claim 14, wherein a plurality of additional guide openings is arranged at a circumference of the core in a level perpendicular in reference to the longitudinal axis in a manner symmetrical over the circumference, and that a plurality of additional guide openings is arranged parallel and at a distance from the longitudinal axis.

22. A device for implementing a method for the production of a single-filament stent from a filament, the device comprising:
- a braiding core having a proximal end section, a distal end section and a first,
- a bobbin having a second axis,
- at least one arm with at least one gripper, the at least one gripper is embodied to engage the filament and to hold the filament,
- the braiding core being arranged around the first axis, and
- the at least one arm and the bobbin being arranged rotationally about the second axis, wherein the at least one gripper comprises a first gripper and a second gripper, the first and second grippers are arranged parallel and at a distance from each other, and are rotational about the second axis, jointly with the bobbin.

23. The device according to claim 22, wherein at least one force sensor is provided by which torque applied to the first axis or the second axis can be determined.

24. The device according to claim 22, wherein the at least one arm is arranged in a manner articulate in reference to the first axis.

25. The device according to claim 22, wherein the first axis and the second axis are aligned parallel in reference to each other or that the first axis and the second axis are aligned perpendicular to each other.

26. The device according to claim 22, wherein at least one holding means is provided, which can apply a holding force upon the braiding core.

27. The device according to claim 26, wherein the at least one holding means is rotational about the first axis.

* * * * *